(12) United States Patent
Talbiersky et al.

(10) Patent No.: US 6,846,962 B2
(45) Date of Patent: Jan. 25, 2005

(54) SELECTIVE PRODUCTION OF O-ALKYLPHENOLS

(75) Inventors: Jörg Talbiersky, Dorsten (DE); Edgar Fuhrmann, Castrop-Rauxel (DE); Wolfgang Brüggemann, Castrop-Rauxel (DE)

(73) Assignee: Rutgers Chemicals AG, Castrop-Rauxel (DE)

(*) Notice: Subject to any disclaimer, the term of this patent is extended or adjusted under 35 U.S.C. 154(b) by 0 days.

(21) Appl. No.: 10/480,497

(22) PCT Filed: Nov. 15, 2002

(86) PCT No.: PCT/EP02/12789

§ 371 (c)(1),
(2), (4) Date: Dec. 11, 2003

(87) PCT Pub. No.: WO03/043965

PCT Pub. Date: May 30, 2003

(65) Prior Publication Data

US 2004/0158104 A1 Aug. 12, 2004

(30) Foreign Application Priority Data

Nov. 21, 2001 (DE) ........................................ 101 57 073

(51) Int. Cl.$^7$ .............................................. C07C 37/00
(52) U.S. Cl. ...................... 568/804; 568/781; 568/789
(58) Field of Search ................................ 568/804, 781, 568/789

(56) References Cited

U.S. PATENT DOCUMENTS 3,737,466 A  6/1973  Sharp et al.

FOREIGN PATENT DOCUMENTS

DE 27 56 461 A1 6/1979
SU 1671655 A1 * 8/1991 ........... C07C/37/14

* cited by examiner

Primary Examiner—Michael L. Shippe
(74) Attorney, Agent, or Firm—Amster, Rothstein & Ebenstein LLP

(57) ABSTRACT

In a method for the production of o-alkyl phenols by conversion of phenol with an alkanol at elevated temperature in the gas phase in the presence of a metal catalyst, the conversion takes place in at least two stages wherein the alkanol/phenol molar ratio in each reaction stage is set to a value of approximately $\leq 0.4$; a clear increase in the selectivity for the o-alkyl phenol is obtained.

9 Claims, No Drawings

SELECTIVE PRODUCTION OF O-ALKYLPHENOLS

This application is a national stage entry under 35 U.S.C. §371 of PCT International Application No. PCT/EP02/12789, filed Nov. 15, 2002, which claims priority of German Patent Application No. 101 57 073.2, filed Nov. 21, 2001.

The invention relates to a multistage method for the o-alkylation of phenol by conversion of phenol with an alkanol at elevated temperature in the gas phase in the presence of an acidic metal oxide catalyst.

Pure o-alkyl phenols are important compounds which are used in large quantities as starting material for organic chemical syntheses. Pure o-cresol (2-methyl phenol) is especially used for the production of pesticides.

o-cresol can be obtained by methylation of phenol with methanol in the gas or liquid phase. As a result of the low reactivity of methanol, the conversion takes place at elevated temperature in the presence of a catalyst. Metal oxide catalysts such as aluminium oxide, silicon dioxide/aluminium mixed oxide and magnesium oxide are used as catalysts. The choice of reaction temperature is made as a function of the catalyst used in a range of 250 to 460° C. Thus, magnesium oxide exhibits a high selectivity for o-cresol in a temperature range of 420 to 460° C. whereas γ-aluminium oxide catalyses the methylation of phenol at a temperature of 200 to 400° C.

Also known is the production of o-cresol as a side product in the synthesis of 2,6-dimethyl phenol and the subsequent isolation of o-cresol by additional purification steps. Methods for the production of o-cresol with further evidence are described in H. G. Franck, J. W. Stadelhofer, INDUSTRIELLE AROMATENCHEMIE, p. 170–177, SPRINGER VERLAG 1987.

DE 27 56 461 A1 describes a generic method which is carried out at a temperature of 250 to 330° C. using alumina as the catalyst. An o-cresol yield of up to 26% is obtained with a methanol to phenol ratio of 0.5:1. The product contains an approximately 6% fraction of 2,6-dimethyl phenol.

At high phenol conversions high fractions of 2,6-dimethyl phenol are always obtained in addition to o-cresol. It is difficult to obtain o-cresol selectively by the methylation of phenol. Considerable quantities of m-cresol and p-cresol or higher alkylated products usually occur as side products.

The high fraction of side products is common to all known methods for the industrial synthesis of o-alkyl phenols.

The object of the invention is thus to provide a method for the production of o-alkyl phenol which is as selective as possible and can be carried out on an industrial scale.

This object is achieved by o-alkylation of phenol with an alkanol at elevated temperature in the gas phase in the presence of a metal oxide catalyst, in which the conversion is carried out in at least two reaction stages and the alkanol/phenol molar ratio is maintained at approximately ≦1 over the entire method.

The method according to the invention can be carried out, for example, in two to five stages. The method takes place especially preferably in three stages. Each conversion stage can be carried out in a different reactor. However, it is also possible to carry out several reaction stages in a single reactor. In this procedure several configurations of the active catalyst separated spatially from one another are accommodated in the reactor. Between the catalyst configurations can be arranged zones with catalyst of lower activity or without catalyst.

The work forming the basis of this invention has shown that anisole is formed during the methylation of phenol and o-cresol is formed, on the one hand, by alkylation of phenol with anisole and, on the other hand, by intramolecular rearrangement of anisole to o-cresol. This finding is new and contradicts the findings so far. The newly discovered reaction sequence is shown in FIG. 1.

It has surprisingly been found that multistage implementation of the method under the afore-mentioned conditions yields a significantly enhanced selectivity of the reaction for o-cresol and an associated increase in the yield of this compound. It is assumed that the high selectivity for o-alkylations is achieved by the low local concentrations of methanol and therefore also of anisole, required in this procedure. It is advantageous that the highly exothermic reaction can be much better controlled by distribution over two, especially three reactors. The formation of so-called hot spots is thereby suppressed.

As a result of the multistage execution of the reaction, the alkanol to phenol ratio in each reactor or in each reaction stage can be set especially low. The phenol conversion is thereby limited and a particularly high selectivity for the o-alkyl phenol, for example, o-cresol can be achieved. The molar ratio of alkanol to phenol over the entire method is preferably set to 0.9, especially preferably to 0.6 or a value in between. Thus, the molar ratio of alkanol to phenol in a three-stage process is preferably 0.3 to 0.2 in each reaction stage.

Expressed alternatively, the phenol conversion can be set to a value of approximately 35 to 43%, for example, 38 to 42% in order to achieve the desired high selectivity.

Suitable catalysts for implementing the method according to the invention are acid metal oxides and their mixtures. Such metal oxides are, for example, aluminium oxide, silicon dioxide/aluminium mixed oxide and magnesium oxide. Especially preferable is γ aluminium oxide. The surface area of the catalysts is preferably approximately 250 $m^2$/g and more, especially preferably 250 to 300 $m^2$/g. These catalysts are produced by known methods, for example, by ammoniacal hydrolysis of aluminium nitrate and subsequent separation, drying and calcination of the precipitate obtained (J. Amer. Chem. Soc. 82 (1960) 2471).

The catalyst can be arranged in the usual form, for example, as a fixed bed, fluid bed or fluidized bed. The catalyst is preferably arranged in a fixed bed.

Alkanols to be used according to the invention are especially $C_{1-4}$ alkanols, i.e., methanol, ethanol, n-propanol, isopropanol, n-butanol and isobutanol.

The method according to the invention can be implemented in a temperature range of 250 to 400° C. When γ aluminium oxide is used as the catalyst, the temperature in the reactor is preferably 300 to 400° C., especially preferably 300 to 340° C., for example, 330° C.

An embodiment of the method according to the invention using methanol as the alkylation agent is described subsequently as an example. The method is carried out in three stages.

For this purpose phenol is fed into a mixer/vaporiser via a metering device. Methanol is supplied to the same mixer/vaporiser via a metering device. The mixture of initial compounds is fed into a tubular reactor heated to 330° C. The flow from the reactor contains the initial compound phenol as well as the products and can be withdrawn at the bottom of the reactor. The flow is fed to another mixer/vaporiser which is positioned before another tubular reactor. The methanol/phenol ratio required for the method according to the invention is adjusted again in this mixer and the mixture obtained is fed into the second reactor. The flow from the second reactor is either fed into a cooler or into a third mixer/vaporiser which is connected before a third reactor. The methanol/phenol ratio required for the method according to the invention is adjusted again in the third reactor and the mixture obtained is fed into the third reactor.

The flow from the third reactor, if appropriate, from the second reactor, is condensed in a cooler and the condensate is fed to a tank.

The processing of the raw alkylate can preferably take place by continuous rectification in a system consisting of three distillation columns connected one behind the other.

In the first column with, for example 20 to 35 practical plates which are operated at normal pressure, the reaction water is separated at the head of the column at a head temperature of 90 to 100° C. The water contains small amounts of phenol, alkyl phenols and anisole since these compounds distill azeotropically with the water.

The sump of the first column is fed continuously into the second column. This column has approximately 100 practical plates and is also operated at normal pressure. At the head of the column phenol with small fractions of o-cresol is withdrawn at a head temperature of 180 to 185° C. This mass flow can be supplied to the alkylation stage again as raw material.

The phenol-free sump of the column 2 continually enters the feed to the third column with approximately 70 to 95 practical plates at 300 mbar head pressure and approximately 145 to 155° C. head temperature. Pure o-cresol having a purity of >99.5% can be drawn off at the head of the column.

The sump of the column which contains small fractions of o-cresol, can be used as raw material to produce cresol/xylenol mixtures.

o-alkylated compounds to be obtained according to the invention are cresol and the ethyl, n-propyl, isopropyl, n-butyl and isobutyl derivatives of phenol.

The following examples serve to explain the invention in greater detail.

EXAMPLE 1

It is known from the literature that anisole forms o-cresol by intramolecular rearrangement. For this reason it was taken as the starting point that a high concentration of anisole should be built up to enhance the product yield. For this purpose pure anisole was fed into a tubular reactor at a temperature of 330° C. at an LHSV (liquid hourly space velocity) of 1.25 $h^{-1}$ in a single-stage method. A γ aluminium oxide with a surface area of approximately 250 $m^2/g$ is used as the catalyst. The products obtained and their concentration in the product mixture are given in the following Table 1.

TABLE 1

| Compound | Concentration % |
| --- | --- |
| Anisole | 7.1 |
| Phenol | 32.2 |
| o-cresol | 28.6 |
| 2,6-xylenol | 16.1 |
| 2,3,6-trimethyl phenol | 4.0 |
| Pentamethyl phenol | 3.3 |
| Anisole conversion | 92.9% |
| o-cresol selectivity | 30.8% |

The results in the table show that anisole with a 92.9% conversion is highly reactive under the selected conditions. The concentration of phenol and higher alkylated phenols such as 2,6-xylenol and 2,3,6-trimethyl phenol shows that only a portion of the anisole is rearranged into o-cresol. Most of the anisole reacts as an alkylation agent.

In order to confirm this supposition, an alkylation experiment was carried out under the same conditions as those described previously, in which methanol was completely replaced by anisole. The results obtained are given in Table 2.

TABLE 2

| | Alkylation agent | |
| --- | --- | --- |
| Compound | Anisole Concentration % | Methanol Concentration % |
| Anisole | — | — |
| Phenol | 76.8 | 72.3 |
| o-cresol | 18.8 | 20.5 |
| 2,6-xylenol | 2.6 | 3.8 |
| 2,3,6-trimethyl phenol | — | 0.4 |
| o-cresol selectivity | 81.0% | 74.0% |

The values show that the behaviour of methanol is similar to that of anisole. The use of anisole even shows a somewhat higher selectivity than when methanol is used as the alkylation agent.

It can be postulated that the selectivity for o-cresol is approximately the same for both alkylation agents. The slightly higher o-cresol selectivity of anisole will be attributable to the fact that the rearrangement of anisole to form o-cresol takes place at the same time as the alkylation of phenol by anisole.

In order to study the fraction of o-cresol which is produced by intramolecular rearrangement, the same experiment was carried out using 4-methyl anisole as the model substance. The concentration of the individual products in the product mixture [%] and the 4-methyl anisole conversion are given in Table 3.

TABLE 3

| Compound | Concentration % |
| --- | --- |
| Phenol | 57.7 |
| o-cresol | 12.8 |
| p-cresol | 18.6 |
| 2,6-xylenol | 1.5 |
| 2,4-xylenol | 6.4 |
| 4-methyl anisole conversion | 100% |

The results show that in addition to o-cresol, significant concentrations of p-cresol and 2,4-xylenol were obtained. p-cresol is formed when 4-methyl anisole acts as an alkylation agent. 2,4-xylenol is the product of the intramolecular rearrangement of 4-methyl anisole. The calculation shows that approximately 70% of the 4-methyl anisole acts as an alkylation agent and approximately 30% is rearranged to form 2,4-xylenol. It is assumed that when anisole is used as the alkylation agent, the same ratios exist.

EXAMPLE 2

Phenol was pumped with methanol into the reactor at a reactor temperature of 330° C. with a methanol/phenol molar ratio of 0.2 and an LHSV of 3.75 $h^{-1}$. An γ aluminium oxide with a surface area of approximately 250 $m^2/g$ is used as the catalyst. In the following second stage methanol was supplied in the molar ratio of 0.2 to the flow from the first stage and the alkylation continued. A similar procedure was adopted to carry out the third alkylation stage.

For comparison, phenol with methanol was converted in a single-stage tubular reactor at a reaction temperature of 330° C. with a methanol/phenol molar ratio of 0.6 at an LHSV of 1.25 h$^{-1}$. The same catalyst was used. In total the methanol/phenol ratio and the LHSV is thus the same as in the three-stage reaction. The product concentration in the product mixture, the phenol conversion and the selectivity for o-cresol for both reactions are given in Table 4.

TABLE 4

| Compound | Single-stage alkylation | Three-stage alkylation |
| --- | --- | --- |
| Anisole | 0.02 | 0.9 |
| Phenol | 53.7 | 58.6 |
| o-cresol | 27.9 | 29.4 |
| m/p-cresol | 1.5 | 0.8 |
| 2,6-xylenol | 9.5 | 6.8 |
| 2,4/2,5-xylenol | 2.0 | 0.9 |
| 2,3,6-trimethyl phenol | 1.7 | 0.9 |
| Phenol conversion | 46.3 | 41.4 |
| o-cresol selectivity | 60.3 | 71.1 |

These results show that in the multistage method the selectivity for o-cresol is significantly higher than in the single-stage method although the phenol conversion in the three-stage method is similar. The reason for this is that the quantity of side products in the single-stage method is significantly higher than that in the three-stage method. Although the anisole content of 0.9% in this experiment is not yet optimal, an increase in the selectivity for o-cresol from 60.3% in the single-stage method to 71.1% in the three-stage method is obtained.

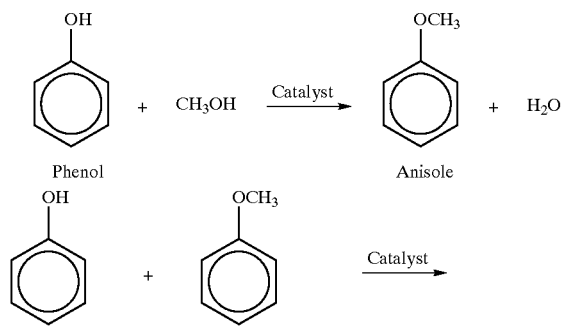

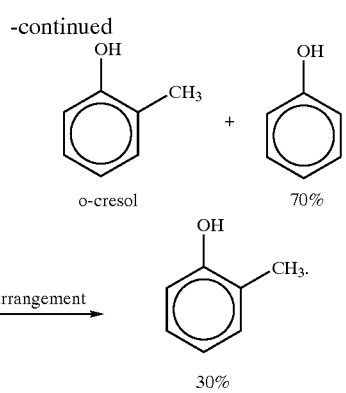

What is claimed is:

1. A method for production of o-alkyl phenols by conversion of phenol with an alkanol at elevated temperature in the gas phase in the presence of a metal catalyst, characterized in that the conversion is carried out in at least two stages and the alkanol/phenol molar ratio in each reaction stage is set to a value of approximately ≦0.4.

2. The method according to claim 1, characterized in that the conversion is carried out in three stages.

3. The method according to claim 1, characterized in that the alkanol/phenol molar ratio in each reaction stage is set to a value of approximately 0.2 to 0.4.

4. The method according to claim 3, characterized in that the alkanol/phenol molar ratio in each reaction stage is set to a value of approximately 0.3.

5. The method according to claim 1, characterized in that the phenol conversion during the reaction is set to 35 to 43% in each stage.

6. The method according to claim 1, characterized in that methanol is used as alkanol.

7. The method according to claim 1, characterized in that an γ aluminum oxide having a surface area greater than 250 m$^2$/g is used as the catalyst.

8. The method according to claim 7, characterized in that the reaction is carried out in a temperature range of 300 to 400° C.

9. The method according to claim 1, characterized in that the product mixture obtained after alkylation is separated by distillation to obtain the desired product.

* * * * *